United States Patent
Guy et al.

(10) Patent No.: US 9,949,936 B2
(45) Date of Patent: *Apr. 24, 2018

(54) USE OF CANNABINOIDS IN THE TREATMENT OF EPILEPSY

(71) Applicant: GW Pharma Limited, Cambridge (GB)

(72) Inventors: Geoffrey Guy, Cambridge (GB); Stephen Wright, Cambridge (GB); Alice Mead, Cambridge (GB); Charuta Joshi, Iowa City, IA (US); Angus Wilfong, Houston, TX (US)

(73) Assignee: GW Pharma Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,766

(22) Filed: Oct. 4, 2016

(65) Prior Publication Data

US 2017/0246121 A1    Aug. 31, 2017

Related U.S. Application Data

(63) Continuation of application No. 14/741,783, filed on Jun. 17, 2015, now Pat. No. 9,474,726.

(30) Foreign Application Priority Data

Jun. 17, 2014 (GB) .................................. 1410771.8
Apr. 17, 2015 (GB) .................................. 1506550.1

(51) Int. Cl.
| | | |
|---|---|---|
| *A61K 31/05* | (2006.01) | |
| *A61K 31/551* | (2006.01) | |
| *A61K 36/185* | (2006.01) | |
| *A61K 31/4015* | (2006.01) | |
| *A61K 31/444* | (2006.01) | |
| *A61K 31/515* | (2006.01) | |
| *A61K 31/4166* | (2006.01) | |
| *A61K 31/55* | (2006.01) | |
| *A61K 31/27* | (2006.01) | |
| *A61K 31/53* | (2006.01) | |
| *A61K 31/19* | (2006.01) | |
| *A61K 9/00* | (2006.01) | |
| *A61K 9/08* | (2006.01) | |

(52) U.S. Cl.
CPC ............ *A61K 31/05* (2013.01); *A61K 9/0053* (2013.01); *A61K 9/08* (2013.01); *A61K 31/19* (2013.01); *A61K 31/27* (2013.01); *A61K 31/4015* (2013.01); *A61K 31/4166* (2013.01); *A61K 31/444* (2013.01); *A61K 31/515* (2013.01); *A61K 31/53* (2013.01); *A61K 31/55* (2013.01); *A61K 31/551* (2013.01); *A61K 36/185* (2013.01)

(58) Field of Classification Search
CPC ...................................................... A61K 31/05
See application file for complete search history.

(56) References Cited

U.S. PATENT DOCUMENTS

| | | |
|---|---|---|
| 6,949,582 B1 | 9/2005 | Wallace |
| 8,293,786 B2 | 10/2012 | Stinchcomb |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 2006/0039959 A1 | 2/2006 | Wessling |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0270845 A1 | 10/2012 | Bannister et al. |
| 2013/0245110 A1 | 9/2013 | Guy et al. |
| 2013/0296398 A1 | 11/2013 | Whalley et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |

(Continued)

FOREIGN PATENT DOCUMENTS

| | | |
|---|---|---|
| EP | 2448637 | 5/2012 |
| GB | 2384707 | 8/2003 |

(Continued)

OTHER PUBLICATIONS

Devinsky et al., Cannabidiol: Pharmacology and potential therapeutic role in epilepsy and other neuropsychiatric disorders, 2014 Epilepsia, 55(6), 791-802.
International Preliminary Report on Patentability dated Sep. 1, 2017 for Application No. PCT/GB2016/051792.
Petrocellis et al., "Effects of cannabinoids and cannabinoid-enriched Cannabis extracts on TRP channels and endocannabinoid metabolic enzymes," British Journal of Pharmacology (2011) 163 1479-1494.
ElSohly and Gul, "Constituents of Cannabis Sariva,"Chapter 1, Handbook of Cannabis, ed. Roger G. Pertwee, pp. 3-22 (2014).
Etienne de Meijer, "The Chemical Phenotypes (Chemotypes) of Cannabis," Chapter 5, Handbook of Cannabis, ed. Roger G. Pertwee, pp. 89-110 (2014).

(Continued)

*Primary Examiner* — Matthew P Coughlin
(74) *Attorney, Agent, or Firm* — Fish & Richardson P.C.

(57) ABSTRACT

The present disclosure relates to the use of cannabidiol (CBD) for the reduction of total convulsive seizure frequency in the treatment of "treatment-resistant epilepsy" (TRE). In particular, the disclosure relates to the use of CBD of treating TRE when the TRE is Dravet syndrome; myoclonic absence seizures or febrile infection related epilepsy syndrome (FIRES). The disclosure further relates to the use of CBD in combination with one or more anti-epileptic drugs (AEDs).

14 Claims, No Drawings

(56) References Cited

U.S. PATENT DOCUMENTS

| | | |
|---|---|---|
| 2014/0343044 A1 | 11/2014 | Ceulemens |
| 2015/0181924 A1 | 7/2015 | Llamas |
| 2015/0320698 A1 | 11/2015 | Whalley et al. |
| 2015/0359756 A1 | 12/2015 | Guy et al. |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |

FOREIGN PATENT DOCUMENTS

| | | |
|---|---|---|
| GB | 2434097 | 7/2007 |
| GB | 2434312 | 7/2007 |
| GB | 2450753 | 1/2009 |
| GB | 2009/11580 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/083098 | 7/2007 |
| WO | WO 2007/138322 | 12/2007 |
| WO | WO 2008/094181 | 8/2008 |
| WO | WO 2008/129258 | 10/2008 |
| WO | WO 2008/146006 | 12/2008 |
| WO | WO 2009/007697 | 1/2009 |
| WO | WO 2009/007698 | 1/2009 |
| WO | WO 2011/001169 | 1/2011 |
| WO | WO 2011/121351 | 10/2011 |
| WO | WO 2012/093255 | 7/2012 |
| WO | WO 2013/032351 | 3/2013 |
| WO | WO 2015/142501 | 9/2015 |
| WO | WO 2015/184127 | 12/2015 |
| WO | WO 2015/193668 | 12/2015 |

OTHER PUBLICATIONS

David J. Potter, "Cannabis Horticulture," Chapter 4, Handbook of Cannabis, ed. Roger G. Pertwee, pp. 65-88 (2014).
Utah Controlled Substances Advisory Committee Meeting, Nov. 12, 2013, available at https://www.utah.gov/pmn/files/81459.pdf.
"When to Expect Results from CW Hemp Oil", downloaded Sep. 5, 2017, https://www.cwhemp.com/blog/expecting-results-from-hemp.
C.C. de Oliveira, et al., "anticonvulsant activity of B-caryophyllene against pentylenetetrazol-induced seizures," Epilepsy Behav. 56:26-3(2016).
Neto, et al., "The role of polar phytocomplexes on anticonvulsant effects of leaf extracts of Lippia alba (Mill.) N.E. Brown chemotypes," J. Pharm Pharmacol. 61(7):933-9 (2009).
Crespel, et al., "Lennox-Gastaut Syndrome," Chapter 14, in Epileptic Syndromes in Infancy, Childhood, and Adolescence, 5th Edition, ed. M. Bureau, et al., pp. 189-216, 1993.
A. Wallace, et al., "Pharmacotherapy for Dravet Syndrome," Pediatr. Drugs, 18:197-208 (2016).

M.M. Gedde, "Clinical Experience with Cannabis in Treatment-Resistant Pediatric Epilepsy," http://www.theroc.us/images/gedde_presentation.pdf, Sep. 9-11, 2014.
E.C. Rosenberg, et al., "Cannabinoids and Epilepsy," Neurotherapeutics, 12(4): 747-768 (2015).
B.C. Kahan, et al. "Risk of selection bias in randomized trials," Trials, 16: 405 (2015).
Lieu et al., "Assessment of self-selection bias in a pediatric unilateral hearing loss study," Otolaryngol Head Neck Surg. 142(3): 427-433 (2010).
Bipolar Health Group (Charlotte's Web Hemp Remedy, available online at http:/bipolarhealthgroup.org/index.php/charlottes-web-hemp-remedy/, accessed Sep. 6, 2017.
Thurstone (Avoid Charlotte's Web for Epilepsy, available online at http://drthurstone.com/charlotted-web-not-safest-option-epiliepsy-treatment/, published Jun. 26, 2014.
Martin, A.R. NIDS research monograph, (1987) vol. 79, pp. 48-58.
Manno, "Status Epilepticus: Current Treatment Strategies," The Neurohospitalist. Jan. 2011, 1(1):23-31.
FDA, "Warning Letters and Test Results for Cannabidiol-Related Products," 2015 Warning Letters Retrieved from: https://www.fda.gov/newsevents/publichealthfocus/ucm484109.htm.
FDA, "Warning Letters and Test Results for Cannabidiol-Related Products," 2016 Warning Letters Retrieved from: https://www.fda.gov/newsevents/publichealthfocus/ucm484109.htm.
Dulac, "Use of Lamotrigine in Lennox-Gastaut and Related Epilepsy Syndromes," J. Child Neurolog., 12(Supplement 1), S23-S29 (1997).
Dulac, "Vigabatrin in Childhood Epilepsy," J. Child Neurolog., 6(Supplement 2), S30-S37 (1991).
IUPHAR/BPS Guide to Pharmacology, Entry for Δ9-tetrahydrocannabidiol, available at http://www.guidetopharmacology.org/GRAC/LigandDisplayForward?tab=biology&ligandId=2424.
Marinol Label Retrieved from: https://www.accessdata.fda.gov/drugsatfda_docs/label/2006/018651s025s0261bl.pdf, 2006.
Guerrini et al., "Lamotrigine and Seizure Aggravation in Severe Myoclonic Epilepsy," Epilepsia, 39(5):508-512, 1998.
Miller et al., "Mapping genetic modifiers of survival in a mouse model of Dravet syndrome," Genes, Brain and Behavior (2014) 13: 163-172.
Stafstrom et al., "Models of Pediatric Epilepsies: Strategies and Opportunities," Epilepsia, vol. 47, No. 8, 2006.
Yu et al., "Reduced sodium current in GABAergic interneurons in a mouse model of severe myoclonic epilepsy in infancy," Nature Neuroscience vol. 9 No. 9 Sep. 2006 pp. 1142-1149.
Van Rijckevorsel, Neuropsychiatr Dis Treat. Dec. 2008; 4(6): 1001-1019.
Brown et al., Child Neurology Foundation, "LGS" (Lennox-Gastaut Syndrome), available at http://www.childneurologyfoundation.org/disorders/lgs-lennox-gastaut-syndrome.
Löscher W, Schmidt D. "Modem antiepileptic drug development has failed to deliver: ways out of the current dilemma." Epilepsia. Apr. 1, 2011, 52(4):657-78.
Bertram, "The Relevance of Kindling for Human Epilepsy," Apr. 1 2007, 48(s2):65-74.
Klitgaard H, Matagne A, Gobert J, Wülfert E. "Evidence for a unique profile of levetiracetam in rodent models of seizures and epilepsy." European journal of pharmacology. Jul. 24, 1998, 353(2):191-206.
Declaration of Professor H. Steve White in the Inter Partes Review of U.S. Pat. No. 9,066,920, Dated Oct. 24, 2017, 69 pages.
[No Author Listed] "Cannabidiol for Aicardi Syndrome," Salutaris., Retrieved on Feb. 10, 2017, Retrieved from the internet: URL http://web.archive.org/web/20141012220050/http://salutarisdrops.com/cannabidiol-aicardi-syndrome/, © 2014, 3 pages.
[No Author Listed] "Cannabidiol Therapy for Aicardi Syndrome" Aug. 2014, 4 pages.
[No Author Listed] "Cannabinoid," Wikipedia., Retrieved on Mar. 1, 2017, Retrieved from Internet: URL https://en.wikipedia.org/wiki/Cannabinoid, 15 pages.
[No Author Listed] "Convulsive Disorders and Their Interference with Driving," Medicos., Retrieved Feb. 10, 2017, Retrieved from internet: URL https://www.medicosporlaseguridadvial.com/en/

(56) References Cited

OTHER PUBLICATIONS clinical-subjects/neurologic-diseases/convulsive-disorders-and-their-interference-with-driving/, 2014, 3 pages.
[No Author Listed] "Estimating the maximum Safe Starting Dose in Initial Clinical Trials for Therapeutics in Adult Healthy Volunteers," *FDA Guidance for Industry.*, Jul. 2005, 30 pages.
[No Author Listed] "GW Pharmaceuticals Announces Epidiolex(R) Receives Fast Track Designation from FDA for the Treatment of Dravet Syndrome." *GW Pharmaceuticals Press Release.*, dated Jun. 6, 2014.
[No Author Listed] "GW Pharmaceuticals Announces Physician Reports of Epidiolex(R) Treatment Effect in Children and Young Adults with Treatment-resistant epilepsy from Physician—Led Expanded Access Treatment Program," *GW Pharmaceutical Press Release.*, dated Jun. 17, 2014.
[No Author Listed] "GW Pharmaceuticals Provides Update on Orphan Program in Childhood Epilepsy for Epidiolex™,"*GW Pharm.*, Available online Nov. 14, 2013, Retrieved Feb. 10, 2017, Retrieved from the internet: URL http://www.gwpharm.com/GW%20Phannaceuticals%20Provides%20Update%20on%20orphan%20Program%20in%20Childhood%20Epilepsy%20for%20Epidiolex.aspx, 5 pages.
[No Author Listed] "GW Pharmaceuticals Receives Orphan Drug Designation by FDA for Epidiolex®in the Treatment of Lennox-Gastaut Syndrom ,"*GW Pharm.*, Available online Feb. 28, 2014, Retrieved Feb. 10, 2017, Retrieved from the internet: URL http://www.gwpharm.com/about-us/news/gw-pharmaceuticals-receives-orphan-drug-designation-fda-epidiolex%C2%AE-treatment-lennox, 4 pages.
[No Author Listed] "Orphan Drug Designation Granted for Epidiolex in Dravet syndrome by the FDA—Seven Expanded Access INDs granted by FDA to US physicians to treat with Epidiolex 125 children suffering from intractable epilepsy syndromes,"*GW Pharmaceuticals Press Release.*, dated Nov. 14, 2013, 3 pages.
[No Author Listed] "What are the Highest CBD Strains?" accessed Feb. 16, 2017, available online at www.leafscience.com, published Oct. 15, 2014, 2 pages.
Alger, "Not Too Excited? Thank Your Endocannabinoids," *Neuron.*, 51(4):393-395, Aug. 17, 2006.
Ames et al., "Anticonvulsant effect of cannabidiol," *S. Afr Med. J.*, 69(1):14, Jan. 4, 1986.
Annex to the Communication-Opposition for Application No. 10734541.5, dated Jan. 28, 2016, 5 pages.
Arain et al., "Pregabalin in the Management of Partial Epilepsy,"*Neuropsychiatr Dis Treat.*, 5:407-413. Epub Aug. 20, 2009.
Avoli et al., "Cellular and molecular mechanisms of epilepsy in the human brain," *Prog Neurobiol.*, 77(3):166-200, 2005.
Bakhsm, Miftaah-al-Khazaain, 1930: 607-8. Urdu. Exhibit 3.
Bancaud et al., "Proposal for Revised Clinical and Electroencephalographic Classification of Epileptic Seizures," *Epilepsia.*, 22(4):489-501, Aug. 1981.
Benowitz et al., "Metabolic and Psychophysiologic studies of cannabidiol hexabarbital interaction," *Clin Pharmacol Ther.*, 28(1):115-120, 1980.
Bhatt et al., "Indigenous Plants in Traditional Healthcare System in Kedamath Valley of Western Himalaya," *Indian J Tradit Knowl.*, 7(2):300-310, Apr. 2008.
Bhattacharyya et al., "Modulation of mediotemporal and ventrostriatal function in humans by Delta9-tetrahydrocannabinol: a neural basis for the effects of Cannabis sativa on learning and psychosis," *Arch Gen Psychiatry.*, 66:442-451, 2009.
Booth et al., "Legalization's opening of medical pot research is a dream and nightmare," *Denver Post.* Dec. 14, 2013.
Bostanci et al., "The effects of octanol on penicillin induced epileptiform activity in rats: An in vivo study," *Epilepsy Res.*, 71(2-3):188-194, Jul. 27, 2006.

Braida et al., "Post-ischemic treatment with cannabidiol prevents electroencephalographic flattening, hyperlocomotion and neuronal injury in gerbils" *Neuroscience Letters.*, 346:61-64, 2003.
Brust et al., "Marijuana use and the risk of new onset seizures." *Trans Am Clin Climatol Assoc.*, 103:176-181, 1992.
Carlini et al., "Hypnotic and Antiepileptic Effects of Cannabidiol," *J Clin Pharmacol.*, 21(8-9 Suppl):417S-427S. Aug.-Sep. 1981 Abstract only.
Castel-Branco et al., "The Maximal Electroshock Seizure (MES) Model in the Preclinical Assessment of Potential New Antiepileptic Drugs," *Methods Find Exp Clin Pharmacol.*, 31(2); 101-106, 2009.
Catherine Jacobsen et al: "Survey of Current Cannabidiol Use in Pediatric Treatment-Resistant Epilepsy", Apr. 22, 2013 (Apr. 22, 2014), XP055238831, Retrieved from the Internet: URL:https://www.theint.com/uploads/1 /9/3/7/1937199/cannabidiol_use_in_pediatric_epilepsy.pdf.
Chiron, C. et al, *Epilepsia*, 2011, vol. 52 Suppl. 2, pp. 72-75.
Chiu et al., "The Influence of Cannabidiol and Δ9-Tetrahydrocannabinol on Cobalt Epilepsy in Rats," *Epilepsia.*, 20:365-375, 1979.
Combined Search and Examination Report dated Jan. 4, 2012 for Application No. GB1116789.7.
Combined Search and Examination Report dated Mar. 25, 2011 for Application No. GB1100043.7.
Combined Search and Examination Report dated Sep. 5, 2014 for Application No. GB1414813.4.
Combined Search and Examination Report under Sections 17 and 18(3) for International Application No. GB1121919.3, dated Feb. 29, 2012, 8 pages.
Combined Search and Examination Report under Sections 17 and 18(3) for International Application No. GB1410771.8, dated Feb. 27, 2015, 7 pages.
Combined Search and Examination Report under Sections 17 and 18(3) for International Application No. GB1418166 3, dated Jul. 2, 2015, 8 pages.
Combined Search and Examination Report under Sections 17 and 18(3) for International Application 1 No. GB1418170.5, dated Jul. 2, 2015, 6 pages.
Combined Search and Examination Report under Sections 17 and 18(3) for International Application No. GB1418171.3, dated Jun. 29, 2015, 8 pages.
Combined Search and Examination Report under Sections 17 and 18(3) for International Application No. GB1506550.1. dated Feb. 5, 2016, 9 pages.
Communication of a Notice of Opposition for Application No. 10734541.5, dated Dec. 17, 2014, 1 page.
Communication Pursuant to Artilce 94(3) EPC in European Patent Application No. 10734541.5, dated Oct. 23, 2012, 3 pages.
Consroe et al., "Anticonvulsant drug antagonism of Δ9tetrahydrocannabinol-induced seizures in rabbits," *Res Commun Chem Pathol Pharmacol.*, 16(1):1-13, Jan. 1977.
Consroe et al., "Anticonvulsant Interaction of Cannabidiol and Ethosuximide in Rats," *J. Pharm. Pharmac.*, 29(8):500-501, Aug. 1977.
Consroe et al., "Anticonvulsant Nature of Marihuana Smoking,"*JAMA.*, 234(3):306-307, Oct. 20, 1975.
Consroe et al,, "Cannabidiol—Antiepileptic Drug Comparisons and Interactions in Experimentally Induced Seizures in Rats," *J. Pharm. Exp. Therap.*, 201(1):26-32, Apr. 1977.
Consroe et al., "Effects of Cannabichol on Behavioral Seizures Caused by Comulsant Drugs or Current in Mice," 83(3-4):293-298, Sep. 24, 1982.
Consroe et al., "Therapeutic Potential of Cannabinoids in Neurological Disorders." Chapter 2, pp. 21-49, Cannabinoids as Therapeutic Agents, R. Mechoulam, ed., CRC Press, Boca Raton (1986).
Consroe et al., Chapter 12, "Potential Role of Cannabinoids for Therapy of Neurological Disorders," p. 459 in Marijuana/Cannabinoids: Neurobiology and Neurophysiology, ed. L. Murphy (1992).
Cortesi et al., "Potential therapeutical effects of cannabidiol in children with pharmacoresistant epilepsy," *Med Hypotheses.*, 68(4):920-921, 2007.

(56) References Cited

OTHER PUBLICATIONS

Cortez et at., Chapter 10 "Pharmacologic Models of Generalized Absence Seizures in Rodents," *Models Seizures Epilepsy.*, 111-126, 2006.
Cunha et al., "Chronic Administration of Cannabidiol to Healthy Volunteers and Epileptic Patients," Pharmacology,. 21(3):175-185 (1980).
Czapinski et at., "3-17-08 Randomized 36-month comparative study of valproic acid (VPA), phenytoin (PHT), phenobarbital (PB) and carbamazepine (CBZ) efficacy in patients with newly diagnosed epilepsy with partial complex seizures," *J. Neural. Sci.*, 150(1):S162-S163, Sep. 1997.
Dasa et al., Brhat Nighantu Ratnakara (Saligramanighantubhusanam. vol. IV. 1997:170. y Sanskrit. Exhibit 5.
Davis et al., "A Predominant Role for Inhibition of the Adenylate Cyclase/Protein Kinase A Pathway In ERK Activation by Cannabinoid Receptor 1 in NIE-115 Neuroblastoma Cells," *J Biol Chem.*, 278(49):48973-80, Dec. 5, 2003.
Davis et al., "Antiepileptic action of marijuana-active substances," *Federation Proceedings.*, 8:284-285, 1949.
Decision in Opposition proceedings (Art. 101(3)(a) and 106(2) EPC in European Patent Application No. EP2448637, dated Dec. 15, 2016, 91 pages.
Declaration of Professor Anthony G. Marson in the Inter Partes Review of U.S. Pat. No. 9,066,920, dated Dec. 13, 2016, 28 pages.
Declaration of Professor Leslie Benet in the Inter Partes Review of U.S. Pat. No. 9,066,920, dated Nov. 22, 2016, 18 pages.
Deshpande et al., Cannabinoid CBI Receptor Antagonists Cause Status Epilepticus-like Activity in the Hippocampal Neuronal Culture Model of Acquired Epilepsy, *Neurosci Lett.*, 411(1):11-6, Jan. 2007.
Dravet, "The core Dravet syndrome phenotype," *Epilelsia.*, 52 Suppl 2:3-9, Apr. 2011.
Dreifus et al., "Proposal for Revised Clinical and Electroencephalographic Classification of Epileptic Seizures," *Epileptsie.* 22:489-501, 1981.
Drugs of the Future, 39(1): 49-56, Jan. 2014 notes Orphan Drug designation for CBD for Lennox-Gastaut Syndrome.
Eadie, "Shortcomings in the current treatment epilepsy," *Expert Rev Neurother.*, 12(12):1419-1427, Dec. 2012.
Eggers, "Temporal lobe epilepsy is a disease of faulty neuronal resonators rather than oscillators, and all seizures are provoked, usually by stress," *Med Hypotheses.*, 69(6): 1284-9, 2007.
Engel et al., Chapter 1 "What Should be Modeled," In *Models Seizure Epilepsy.*, 2006, 14 pages.
Engel,"Report of the ILAE Classification Core Group," *Epilepsia.* 47(9):1558-1568, 2006.
Examination Report dated Mar. 18, 2014 for Application No. GB1100043.7.
Fariello, "Parenteral Penicillin in Rats: An Experimental Model of Multifocal Epilepsy," *Epilepsia*, 17:217-222, 1976.
Ferdinand et al., "Cannabis—Psychosis Pathway Independent of Other Types of Psychopathology," *Schizophrenia Research.*, 79:289-295, 2005.
Fisher et al., "The impact of epilepsy from the patients's perspective I. Despriptions and subjective perceptives," *Epilepsy Research.*, 41(1):39-51, 2000.
Gabor et al., "Lorazepam Versus Phenobarbital: Candidates for Drug of Choice for Treatment of Status Epilepticus," *J Epilepsy.*, 3(1):3-6, Jan. 1990.
Gallily et al., "Overcoming the Bell-Shaped Dose-Response of Cannabidiol by Using Caimabis Extract Enriched in Cannabidiol," *Pharmacology & Pharmacy.*, 6:75☐85, Jan. 2015.
Gastaut., "Clinical and Electroencephalographical Classification of Epileptic Seizures," *Epilepsia.*, 11:102-113, 1970.
Gedde, M. et al Epilepsey Currents 2014 Posters excerpt pp. 449-450.
Geffrey et al., "Cannabidiol (CBD) Treatment for Refractory Epilepsy in Tuberous Sclerosis Complex (TSC)," *American Epilepsy Society.*, Annual Meeting Abstracts: View, Abstract 2.427, 2014, retrieved on Feb. 10, 2017, retrieved from the internet; URL <https://www.aesnet.org/meetings_events/annual_meeting_abstracts/view/1868979>, 2 pages.
Green, "CBD: An Unconventional Therapy," available online at http://nugs.com/article/cbd-an-unconventional-therapy.html, published Mar. 24, 2014, 5 pages.
Gresham et al., "Treating Lennox-Gastaut syndrome in epileptic pediatric patients with thirdgeneration rufinamide," *Neuropsychiatr Dis Treat.* 6:639-645, Oct. 5, 2010.
Gross et al., "Marijuana use and Epilepsy: Prevalence in Patients of a Tertiary Care Epilepsy Center," *Neurology.*, 62(11):2095-7. Jun. 8, 2004.
Guimaraes et al., "Antianxiety effect of cannabidiol in the elevated plus-maze," *Psychopharmacology.*, 100:558-559, 1990.
Heinemann et al., "An Overview of In Vitro Seizure Models in Acute and Organotypic Slices," Chapter 4, 35-44, 2006.
Hill et al., "Δ☐-Tetrahydrocannabivarin suppresses in vitro epileptiform and in vivo seizure activity in adult rats," *Epilepsia.*, 51(8):1522-1532, Aug. 2010.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," *ACS Chem. Neurosci.*, 5:1131-1141, Jul. 16. 2014.
International Preliminaly Report on Patentability in International Application No. PCT/GB2010/051066, dated May 3, 2011, 6 pages.
International Preliminary Report on Patentability dated Apr. 18, 2017 for Application No. PCT/GB2015/053030.
International Preliminary Report on Patentability dated Dec. 12, 2013 for Application No. PCT/GB2012/052284.
International Preliminary Report on Patentability dated Jun. 9, 2011 for Application No. PCT/GB2010/051066.
International Search Report and Written Opinion dated Aug. 25, 2015 for Application No. PCT/GB2015/051775.
International Search Report and Written Opinion dated Aug. 26, 2015 for Application No. PCT/GB2015/051775.
International Search Report and Written Opinion dated Dec. 13, 2010 for Application No. PCT/GB2010/051066.
International Search Report and Written Opinion dated May 30, 2011 for Application No. PCT/GB2011/050649.
International Search Report and Written Opinion dated Nov. 16, 2012 for Application No. PCT/GB2012/052284.
International Search Report in International Application No. PCT/GB2010/051066, dated Nov. 16, 2010, 3 Pages.
International Search Report in International Application No. PCT/GB2012/050002, dated Feb. 24, 2012, pages.
Iuvone et al., "Neuroprotective Effect of Cannabidiol, a Non-psychoactive Component From Cannabis Sativa, on Beta-amyloid-induced toxicity in PC12 Cells," *J Neurochem.*, 89(1):134-41, Apr. 2004.
Izzo et al., "Non-psychotropic plant cannabinoids: new therapeutic opportunities from an ancient herb," *Trends in Pharmacological Sciences.*, 30(10):515-527, 2009.
Jeavons et al., "Sodium Calproate in Treatment of Epilepsy," *Br Med J.*, 2(5919):584-6, Jun. 15, 1974.
Jones, et al., "Cannabidiol Displays Antiepileptiform and Antiseizure Properties in Vitro and in Vivo," *J Pharmacol Exp Ther.*, 332(2):559-577, Feb. 2010.
Joy et al., "Marijuana and Medicine Assessing the Science Base", *Instit Med.*, National Academy Press, pp. 125, 170 pages total, 1999.
Karler et al., "The Cannabinoids as Potential Antiepileptics," *J Clin Pharmacol.*, 21:437S-448S, Aug.-Sep. 1981.
Khan et al., Khazaain-al-Adiva. vol. I. 1911:885. Urdu. Exhibit 7.
Khan et al., Khazaain-al-Adiva. vol. I. 1911:886. Urdu. Exhibit 4.
Khan et al., Khazaam-al-Advia, vol. I. 1911: 889. Urdu. Exhibit 3.
Khan et al., Khazaani-al-Advia, vol. I. 1911: 889. Urdu. Exhibit 4.
Khan et al., Muheet-e-Azam, vol. II. 1887: 147. Persian. Exhibit 1.
Klitgaard et al., "Electrophysiological, neurochemical and regional effects of levetiracetam in the rat pilocarpine model of temporal lobe epilepsy," *Seizure.* 12(2):92-100, Mar. 2003.

(56) References Cited

OTHER PUBLICATIONS

Kramer et al., "Febrile infection-related epilepsy syndrome (FIRES): pathogenesis, treatment, and outcome: a multicenter study on 77 children," *Epilepsia.*, 52(11):1956-65, Nov. 2011.
Kwan et al., Definition of drug resistant epilepsy: consensus proposal by the ad hoc Task Force of the ILAE Commission on Therapeutic Strategies. *Epilepsia.*, 51(6):1069-77, Jun. 2010 Erratum in: Epilepsia. 51(9): 1922, Sep. 2010.
Letter from Opponent Regarding Oral Proceedings in European Patent No. EP2448637, dated Oct. 20, 2016, 6 pages.
Lindamood et al., "Effects of Δ9-Tetrahydrocannabinol and Cannabidiol on Sodium-Dependent High Affinity Choline Uptake in the Rat Hippocampus1," *J Pharmacology Experimental Therapeutics.*, 213(2):216-221, 1980.
Long et al., "The Pharmacological actions of cannabidiol," *Drugs of the Future.*, 30(7), 747-753, Jul. 1, 2005.
Lowenstein D.H., Chapter 363, Section 2 "Diseases of the Central Nervous System," *Seizures and Epilepsy.*, 2498-2512, 2008.
Luttjohann et al., "A Revised Racine's scale for PTZ-induced seizures in rats," *Physiology & Behavior.*, 98:579-586, 2009.
Lutz., "On-demand activation of the endocannabinoid system in the control of neuronal excitability and epileptiform seizures," *Biochemical Pharmacology.*, 68(9):1691-1698, Nov. 2004.
Maa et al., "The Case for Medical Marijuana in Epilepsy," *Epilepsia.*, 55(6):783-786, Jun. 2014.
Mackie., "Cannabinoid Receptors as Therapeutic Targets," *Annu Rev Pharmacol Toxicol.*, 46:101-122, 2006.
Majoosi, et al. Kaamil-al-Sena'ah, Part II, Central Council for Research in Unani Medicine. 2005: 116. Arabic. Exhibit 2.
Malfait et al., "The nonpsychoactive cannabis constituent cannabidiol is an oral anti-arthritic therapeutic in murine collagen-induced arthritis," *PNAS.*, 97(17):9561-9566, Aug. 15, 2000.
Mattson et al., "Comparison of carbamazepine, phenobarbital, phenytoin, and primidone in partial and secondarily generalized tonic-clonic seizures," *N Engl J Med.*, 313(3):145-151, Jul. 18, 1985.
Mattson et al., "Prognosis for total control of complex partial and secondary generalized tonic clonic seizures," *Neurology.*, 47:68-76, 1996.
McCormick et al., "On the Cellular Network Bases of Epileptic Seizures," *Annu Rev Physiol.*, 63:815-846, 2001.
Mechoulam et al., "Cannabidiol: An Overview of Some Pharmacological Aspects," *J Clin Pharmacol.*, 42:11S-19S, 2002.
Mechoulam et al., "Toward drugs derived from cannabis," *Naturwissenschaften*, 65(4): 174-179, Apr. 1978.
Merlis., "Proposal for an International Classification of Epilepsies," *Epilepsia.*, 11:114-119, 1970.
Models of Chemically-Induced Acute Seizures 127-152, 2006.
Morad et al., "Conversion to Sirolimus-Based Imunnosuppression in Maintenance Liver Transplantation Patients," *Liver Transplantation.*, 13:658-664, 2007.
Ng et al., "Illicit Drug Use and the Risk of New-Onset Seizures," *Am J Epidemiol.*, 132(1):47-57, 1990.
Notice of Allowance in U.S. Appl. No. 13/380,306, dated Dec. 10, 2014, 5 pages.
Notice of Appeal in in U.S. Appl. No. 13/380 305, dated Mar. 19. 2015. 7 pages.
Notice of Appeal in European Patent No. EP2448637, dated Feb. 14, 2017, 5 pages.
Notice of Opposition to a European Patent No. EP2448637, dated Dec. 5, 2014, 20 pages.
Obay et al., "Antiepileptic effects of ghrelin on pentylenetetrazole-induced seizures in rats," *Peptides.*, 28(6):1214-1219, Jun. 2007
Office Action in U.S. Appl. No. 13/380,305, dated Aug. 25, 2014.
Opponent Response to the Preliminary Opinion of the Opposition Division in European Patent No. EP2448637, dated Jun. 23, 2016, 27 pages.
Opponent Response to the Preliminary Opinion of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3 pages.
Opponent Written Submission in European Patent No. EP2448637, dated Nov. 4, 2016, 3 pages.
Pelliccia et al., "Treatment with CBD in oily solution of drug-resistant paediatric epilepsies," Available online Sep. 2, 2010, Retrieved Jun. 30, 2015, Retrieved from the internet: URL http://www.cannabismed.org/studies/ww_en_db_study_show.php?s_id=173&&search_pattern=EPILEPSY, 2 pages, Abstract only.
Pereira et al., Study pharmacologic of the GABAergic and glutamatergic drugs on seizures and status epilepticus induced by pilocarpine in adult Wistar rats, *Neurosci Lett.*, 419(3):253-7, Jun. 4, 2007.
Pertwee, "Cannabinoid receptor ligands: clinical and neuropharmacological considerations, relevant to future drug discovery and development," *Expert Opin Investig Drugs.*, 9(7): 1553-71, Jul. 2000.
Pertwee, "The diverse CB1 and CB2 receptor pharmacology of three plant cannabinoids: Δ9-tetrahydrocannabinol, cannabidiol and Δ9-tetrahydrocannabivarin," *Br. J. Pharmacol.*, 153(2):199-215, 2008.
Pertwee, Chapter 3. "The Pharmacology and Therapeutic Potential of Cannabidiol," pp. 32-83 in the book Neuroscience Intelligence Unit: Cannabinoids, Ed Vincenzo Di Marzo, Springer Science & Business Media, (2004).
Petition for Inter Partes Review of U.S. Pat. No. 9,066,920, dated Dec. 16, 2016, 77 pages.
Pohl et al., "Effects of flunarizine on Metrazol-induced seizures in developing rats," *Epilepsy Res.*, 1:302-305, 1987.
Porter et al., "Report of a Parent Survey of Cannabidiol-enriched Cannabis use in Pediatric Treatment-resistant Epilepsy," *Epilepsy Behavior.*, 29(3):574-577, Dec. 2013.
Press et al., "Parental reporting of response to oral cannabis extracts for treatment of refractory epilepsy," *Epilepsy Behav.*, 45;49-52, Apr. 2015.
Rauca et al., "The role of superoxide dismutase and a-tocopherol in the development of seizures and kindling induced by pentylenetetrazol—influence of the radical scavenger a-phenyl-N-tert-butyl nitrone," *Brain Research.*, 1009(1-2):203-212, May 29, 2004.
Russo, Taming THC: potential cannabis synergy and phytocannabinoid-terpenoid entourage effects, 163 British J. of Pharm. 1333 (2011).
Reply of the Patent Proprietor to the Notice(s) of Opposition in European Patent No. 2448637, dated May 28, 2015, 12 pages.
Reply to Communication from the Examining Division in European Patent Application No. 10734541.5, dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016 13 pages.
Reply to Opponent's Written Submissions in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Resstel et al., "5-HTIA receptors are involved in the cannabidiol-induced attenuation of behavioural and cardiovascular responses to acute restraint stress in rats," *Br J Pharmacol.*, 156(1): 181-8, Jan. 2009.
Rubio et al., "In Vivo Experimental Models of Epilepsy," *Central Nervous System Agents in Medicinal Chemistry.*, 10:298-309, 2010.
Sadanandasarma et al., Rasatarangini. I Ith Ed. 1979:720-3. Sanskrit. Exhibit 6.
Sander., "The epidemiology of epilepsy revisited," *Curr Opin Neurol.*, 16(2):165-170, Apr. 2003.
Sastri et al., Anandakandam. 1st Edition, 1952:241. Sanskrit. Exhibit 2.

(56) References Cited

OTHER PUBLICATIONS

Scuderi et al., "Cannabidiol in Medicine: A Review of its Therapeutic Potential in CNS Disorders," *Phytother Res.*, 23(5):597-602, May 2009.

Silva, R. et al., Can. J. Neurol. Sci. 2006 vol. 33 pp. 783-786.

Statement of Opposition for EP10734541.5 dated Dec. 5, 2014.

Stott et al., "Cannabinoids for the pharmaceutical industry," *Euphytica.*, 140:83-93, 2004.

Swann., "The Effects of Seizures on the Connectivity and Circuitry of the Developing Brain," *MRDD.*, 10(2):96-100, 2004.

Third Party Observations for Application No. AU2012314128 dated Mar. 19, 2015.

Third Party Observations for Application No. EPI 1712658.1 dated Nov. 22, 2013.

Third Preliminary Amendment under 37 C.F.R. 1.115 in U.S. Appl. No. 13/380,305, dated May 23, 2014, 4 pages.

Thomas et al., "Evidence that the Plant Cannabinoid Δ9-Tetrahydrocannabivarin is a Cannabinoid CBI and CB2 Receptor antagonist," *Br J Pharmacol.*, 146(7):917-926, Dec. 2005.

Thurman et al., "Standards for epidemiologic studies and surveillance of epilepsy," *Epilepsia.*, 52 Suppl 7:2-26, Sep. 2011.

Trembly et al., "Double-blind clinical study of cannabidiol as a secondary anticonvulsant," Marijuana '90 Int. Conf. on Cannabis and Cannabinoids, Kolympari (Crete), Jul. 8-11, 1990, 1 page. Abstract Only.

Turkanis et al., "An Electrophysiological Analysis of the Anticonvulsant Action of Cannabidiol on Limbic Seizures in Conscious Rats," *Epilepsia.*, 20:351-363, 1979.

Usami et al., "Synthesis and Pharmacological Evaluation in Mice of Halogenated Cannabidiol Derivatives," *Chem Pharm Bull.*, 47(11):1641-1645, Nov. 1999.

Velisek., "Models of Chemically-Induced Acute Seizures," *Models Seizure Epilepsy.*, 127-152, 2006.

Veliskova., Chapter 48 "Behavioral Characterization of Seizures in Rates," *Models Seizures Epilepsy.*, 601-611, 2006.

Vollner et al., Haschisch XX: Cannabidivarin, ein neuer Haschisch-Inhaltsstoff, *Tetrahedron Lett.*, 10(3):145-147, 1969.

Wahle et al., "Development of Tolerance to the Anticonvulsant Effect of Valproate but not to Ethosuximide in a Rat Model of Absence Epilepsy," *Eur J Pharma.*, 181(1-2):1-8, May 1990.

Wallace et al., "Assessment of the role of CB1 receptors in cannabinoid anticonvulsant effects," *European J Pharmacology.*, 428(1)51-57, 2001.

Weston et al., "Tetrahydrocannabivarin Exhibits Anticonvulsant Effects in a Piriform Cortical Brain Slice Model of Epileptiform Activity," *Pro British Pharm. Soc.*, Retrieved on Mar. 1, 2017, Retrieved Online: URL http://www.pA2online.org/abstract/abstract.jsp?abid=28533, 1 page, Abstract Only.

Whole-Plant Cannabinoids Outperform Single Molecule Compounds at 1/5, Charlotte's Web: By the Stanley Brothers (Jan. 11, 2017) available at https://www.cwhemp.com/blog/whole-plant-cw-hemp-cannabinoids.

Wingerchuk., "Cannabis for medical purposes: cultivating science, weeding out the fiction," *Lancent.*, 364:315-316, Jul. 24, 2004.

Written Opinion of the International Application No. PCT/GB2010/051066, dated Nov. 22, 2010, 4 pages.

Yuriev, "Endogenic Cannabinoid System is a New Perspective Object to Pharmacotherapeutic Effect of Disease of Nervous System," *Ukrainsky Metodichny Chasopis*, 6(50): 21-9, 2005.

Zhao et al., Chapter 27 "Repetitive Seizures in the Immature Brain," *Models Seizures Epilepsy.*, 341-350, 2006.

Zuardi et al., "Cannabidiol, a Cannabis sativa constituent, as an antipsychotic drug," *Brazilian Journal of Medicine and Biological Research.*, 39(4): 421-429, Apr. 2006.

Zuardi et al., "Cannabidiol: from an inactive cannabinoid to a drug with wide spectrum of action," *Rev Bras Psiquiatr.*, 30(3):271-80 (2008).

Supplemental Expert Statement of Professor Benjamin J. Whalley, dated Nov. 4, 2016, 9 pages.

Expert Statement of Vincenzo Di Marzo for Application No. EP10734541.5, dated Sep. 9, 2016.

Expert Statment of Professor Benjamin J. Whalley for Application No. EP10734541.5, dated Sep. 9, 2016.

Expert Statement of Professor Anthony G Marson for Application No. EP10734541.5, 2016.

Expert Statement of Dr. Emma Louise Cheetham, dated Nov. 4, 2016, 6 pages.

Third Party Observations for Application No. EP10734541.5 dated Apr. 3, 2017.

Holmes et al. "Choosing the Correct AED: From Animal Studies to the Clinic,"Pediatr Neurol. Mar. 2008; 38(3): 151-162.

Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.

Statement of Grounds of Appeal for European Application No. 10734541.5 on behalf of the Proprietors: GW Pharma Limited and Otsuka Pharmaceutical CO Limited, dated Apr. 12, 2017.

Patent Owners' Preliminary Response for IPR2017-00503 dated Apr. 11, 2017, 45 pages.

Decision in IPR2017-00503 dated Jul. 7 2017, 26 pages.

Mares et al., Electrical Stimulation-Induced Models of Seizures in Model of Seizures and Epilepsy (Asla Pitkänen, Philip A. Schwartzkroin & Solomon L. Moshé, eds.), 2004.

USE OF CANNABINOIDS IN THE TREATMENT OF EPILEPSY

RELATED APPLICATION

This application is a continuation of U.S. application Ser. No. 14/741,783, filed Jun. 17, 2015, which claims the benefit of GB 1506550.1and GB 1410771.8, the content of each of which is incorporated by reference herein in its entirety.

FIELD OF THE INVENTION

The present invention relates to the use of cannabidiol (CBD) for the reduction of total convulsive seizure frequency in the treatment of "treatment-resistant epilepsy" (TRE). In one embodiment the patients suffering from TRE are children and young adults. CBD appears particularly effective when the TRE is Dravet syndrome; myoclonic absence seizures or febrile infection related epilepsy syndrome (FIRES). In these indications the reduction of total convulsive frequency has surprisingly been shown to be greater than 50%, through 70% to greater than 90% in a significant number of patients. Indeed a significant number of patients have been seizure free at the end of three months treatment.

Preferably the CBD used is in the form of a highly purified extract of *cannabis* such that the CBD is present at greater than 98% of the total extract (w/w) and the other components of the extract are characterised. In particular tetrahydrocannabinol (THC) has been substantially removed to a level of not more than 0.15% (w/w). Alternatively, it is a synthetically produced CBD.

In use the CBD is used concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from "treatment-resistant epilepsy" (TRE).

Treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

One such childhood epilepsy is Dravet syndrome. Onset of Dravet syndrome almost always occurs during the first year of life with clonic and tonic-clonic seizures in previously healthy and developmentally normal infants (Dravet, 2011). Symptoms peak at about five months of age. Other seizures develop between one and four years of age such as prolonged focal dyscognitive seizures and brief absence seizures.

Seizures progress to be frequent and treatment-resistant, meaning that the seizures do not respond well to treatment. They also tend to be prolonged, lasting more than 5 minutes. Prolonged seizures may lead to status epilepticus, which is a seizure that lasts more than 30 minutes, or seizures that occur in clusters, one after another.

Prognosis is poor and approximately 14% of children die during a seizure, because of infection, or suddenly due to uncertain causes, often because of the relentless neurological decline. Patients develop intellectual disability and lifelong ongoing seizures. Intellectual impairment varies from severe in 50% patients, to moderate and mild intellectual disability each accounting for 25% of cases.

There are currently no FDA approved treatments specifically indicated for Dravet syndrome. The standard of care usually involves a combination of the following anticonvulsants: clobazam, clonazepam, levetiracetam, topiramate and valproic acid.

Stiripentol is approved in Europe for the treatment of Dravet syndrome in conjunction with clobazam and valproic acid. In the US, stiripentol was granted an Orphan Designation for the treatment of Dravet syndrome in 2008; however, the drug is not FDA approved.

Potent sodium channel blockers used to treat epilepsy actually increase seizure frequency in patients with Dravet Syndrome. The most common are phenytoin, carbamazepine, lamotrigine and rufinamide.

Management may also include a ketogenic diet, and physical and vagus nerve stimulation. In addition to anticonvulsive drugs, many patients with Dravet syndrome are treated with anti-psychotic drugs, stimulants, and drugs to treat insomnia.

Common AED defined by their mechanisms of action are described in the following tables:

Examples of Narrow Spectrum AED

| Narrow-spectrum AED | Mechanism |
| --- | --- |
| Phenytoin | Sodium channel |
| Phenobarbital | GABA/Calcium channel |
| Carbamazepine | Sodium channel |
| Oxcarbazepine | Sodium channel |
| Gabapentin | Calcium channel |
| Pregabalin | Calcium channel |
| Lacosamide | Sodium channel |
| Vigabatrin | GABA |

Examples of Broad Spectrum AED

| Broad-spectrum AED | Mechanism |
| --- | --- |
| Valproic acid | GABA/Sodium channel |
| Lamotrigine | Sodium channel |

-continued

| Broad-spectrum AED | Mechanism |
| --- | --- |
| Topiramate | GABA/Sodium channel |
| Zonisamide | GABA/Calcium/Sodium channel |
| Levetiracetam | Calcium channel |
| Clonazepam | GABA |
| Rufinamide | Sodium channel |

Examples of AED Used Specifically in Childhood Epilepsy

| AED | Mechanism |
| --- | --- |
| Clobazam | GABA |
| Stiripentol | GABA |

Over the past forty years there have been a number of animal studies on the use of the non-psychoactive cannabinoid cannabidiol (CBD) to treat seizures. For example, Consroe et al., (1982) determined that CBD was able to prevent seizures in mice after administration of pro-convulsant drugs or an electric current.

Studies in epileptic adults have also occurred in the past forty years with CBD. Cunha et al. reported that administration of CBD to eight adult patients with generalized epilepsy resulted in a marked reduction of seizures in 4 of the patients (Cunha et al., 1980).

A study in 1978 provided 200 mg/day of pure CBD to four adult patients, two of the four patients became seizure free, whereas in the remainder seizure frequency was unchanged (Mechoulam and Carlini, 1978).

In contrast to the studies described above, an open label study reported that 200 mg/day of pure CBD was ineffective in controlling seizures in twelve institutionalized adult patients (Ames and Cridland, 1986).

Based on the fact that chronologically the last study to look at the effectiveness of CBD in patients with epilepsy proved that CBD was unable to control seizures, there would be no expectation that CBD might be useful as an anticonvulsant agent.

In the past forty years of research there have been over thirty drugs approved for the treatment of epilepsy none of which are cannabinoids. Indeed, there appears to have been a prejudice against cannabinoids, possible due to the scheduled nature of these compounds and/or the fact that THC, which is a known psychoactive, has been ascribed as a pro-convulsant (Consroe et al., 1977).

A paper published recently suggested that cannabidiol-enriched *cannabis* may be efficacious in the treatment of epilepsy. Porter and Jacobson (2013) report on a parent survey conducted via a Facebook group which explored the use of *cannabis* which was enriched with CBD in children with treatment-resistant epilepsy. It was found that sixteen of the 19 parents surveyed reported an improvement in their child's epilepsy. The children surveyed for this paper were all taking *cannabis* that was purported to contain CBD in a high concentration although the amount of CBD present and the other constituents including THC were not known. Indeed, whilst CBD levels ranged from 0.5 to 28.6 mg/kg/day (in those extracts tested), THC levels as high as 0.8 mg/kg/day were reported.

Providing children with TRE with a *cannabis* extract that comprises THC, which has been described as a pro-convulsant (Consroe et al., 1977), in even small amounts, let alone at a potentially psychoactive dose of 0.8 mg/kg/day, is extremely dangerous and as such there is a real need to determine whether CBD is in fact efficacious.

To date there have been no controlled trials of CBD in children and young adults with TRE.

BRIEF SUMMARY OF THE DISCLOSURE

In accordance with a first aspect of the present invention there is provided cannabidiol (CBD) for use in the treatment of treatment-resistant epilepsy (TRE), wherein the epilepsy is febrile infection related epilepsy syndrome (FIRES).

In accordance with a second aspect of the present invention there is provided cannabidiol (CBD) for use in the treatment of epilepsy, wherein the epilepsy is a treatment-resistant epilepsy (TRE), and wherein the CBD is present in an amount that reduces total convulsive seizure frequency by greater than 50% with respect to the seizure frequency achieved on concomitant anti-epileptic drugs (AED).

Preferably the CBD is used in combination with two or more concomitant anti-epileptic drugs (AED). The CBD may be formulated for administration separately, sequentially or simultaneously with one or more AED or the combination may be provided in a single dosage form.

Preferably the seizure type to be treated is a complex partial seizure (focal seizure with impairment).

Preferably the CBD is present in an amount that reduces total convulsive seizure frequency by greater than 70% with respect to the seizure frequency achieved on concomitant anti-epileptic drugs (AED). More preferably the CBD is present in an amount that reduces total convulsive seizure frequency by greater than 90% with respect to the seizure frequency achieved on concomitant anti-epileptic drugs (AED). More preferably still the CBD is present in an amount that reduces total convulsive seizure frequency by 100% with respect to the seizure frequency achieved on concomitant anti-epileptic drugs (AED).

In one embodiment the CBD is present as a highly purified extract of *cannabis* which comprises at least 98% (w/w) CBD.

The one or more AED is preferably selected from the group consisting of: clobazam; levetiracetam; topiramate; stiripentol; phenobarbital; lacsamide; valproic acid; zonisamide; perampanel; and fosphenytoin.

Preferably the CBD is used in combination with clobazam.

Preferably the number of different anti-epileptic drugs or the dose of AED that are used in combination with the CBD is reduced. More preferably the dose of AED which is reduced is of clobazam.

Preferably the dose of CBD is greater than 5 mg/kg/day. Thus for a 15 kg patient a dose of greater than 75 mg of CBD per day would be provided. Doses greater than 5 mg/kg/day such as greater than 10/mg/kg/day, greater than 15 mg/kg/day, greater than 20 mg/kg/day and greater than 25 mg/kg/day are also envisaged to be effective.

In accordance with a third aspect of the present invention there is provided a method of treating treatment-resistant epilepsy comprising administering cannabidiol (CBD) to a subject, wherein the epilepsy is febrile infection related epilepsy syndrome (FIRES).

In accordance with a fourth aspect of the present invention there is provided a method of treating treatment-resistant epilepsy comprising administering cannabidiol (CBD) to a subject in an amount sufficient to reduce total convulsive seizure frequency by greater than 50% with respect to the seizure frequency achieved on one or more concomitant anti-epileptic drugs (AED).

DEFINITIONS

Definitions of some of the terms used to describe the invention are detailed below:

The cannabinoids described in the present application are listed below along with their standard abbreviations.

cannabinoid components that are co-extracted with the cannabinoids have been removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

CBD   Cannabidiol

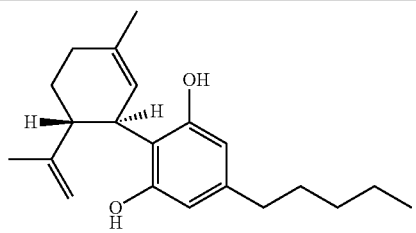 [SMILES: C=C(C)[C@@H]1CCC(C)=C[C@H]1c1c(O)cc(CCCCC)cc1O]

CBDA  Cannabidiolic acid

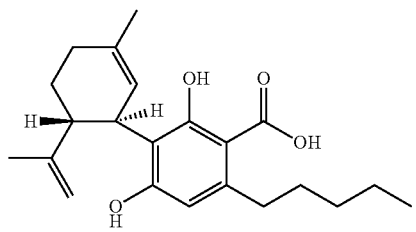 [SMILES: C=C(C)[C@@H]1CCC(C)=C[C@H]1c1c(O)cc(CCCCC)c(C(=O)O)c1O]

CBDV  Cannabidivarin

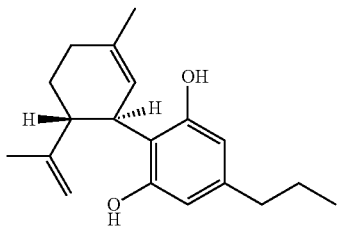 [SMILES: C=C(C)[C@@H]1CCC(C)=C[C@H]1c1c(O)cc(CCC)cc1O]

THC   Tetrahydrocannabinol

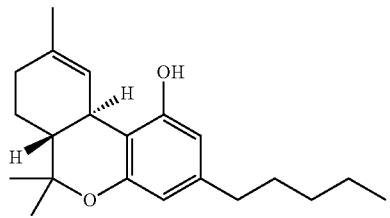 [SMILES: CCCCCc1cc(O)c2c(c1)OC(C)(C)[C@@H]1CCC(C)=C[C@@H]21]

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non- "Treatment-resistant epilepsy" (TRE) is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 1 below.

TABLE 1

CBD Specification

| Test | Test Method | Limits |
| --- | --- | --- |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Impurities (Other Cannabinoids): | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The possible impurities are related cannabinoids: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Examples 1 to 3 below describe the use of a highly purified *cannabis* extract comprising cannabidiol (CBD). Cannabidiol is the most abundant non-psychoactive cannabinoid in the *cannabis* plant. Previous studies in animals have demonstrated that CBD has anticonvulsant efficacy in multiple species and models.

Example 1 describes data produced in an expanded access treatment program in children with TRE.

Examples 2 to 4 demonstrates the efficacy of CBD in children with Dravet syndrome, myoclonic absence seizures and FIRES respectively.

EXAMPLE 1

Efficacy of Cannabidiol in Children and Young Adults with Treatment-Resistant Epilepsy Materials and Methods Twenty-seven children and young adults with severe, childhood onset treatment-resistant epilepsy (TRE) were tested with a highly purified extract of cannabidiol (CBD) obtained from a *cannabis* plant. The participants in the study were part of an expanded access compassionate use program for CBD.

All patients entered a baseline period of 4 weeks when parents/caregivers kept prospective seizure diaries, noting all countable motor seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4, 8 and 12 weeks of CBD therapy.

Results

There were 27 children and young adult patients who received at least 3 months of treatment all of whom suffered from treatment-resistant epilepsy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Co-treatment of CBD with clobazam was a significant predictor of a positive treatment response of greater than 50% responder rate. There was an odds ratio (OR) of 3.3 for total seizure reduction and of 1.9 for convulsive seizures. The OR evaluates whether the odds of a certain event or outcome is the same for two groups. Specifically, the OR measures the ratio of the odds that an event or result will occur to the odds of the event not happening. An OR greater than 1 signifies that patients treated with a combination of CBD with clobazam will have a better odds of having a positive reduction in seizures than if they were not taking this combination of medications.

The median number of seizures that these patients suffered from before starting treatment was 30 seizures per month, with a range of 4 to 2,800 seizures per month being recorded.

Efficacy results for the 27 patients are summarized in Table 2 below.

Table 2 shows that after 3 months of therapy, 48% of patients had an equal to or greater than >50% reduction in seizures.

Remarkably, two of the patients, equating to 7%, were entirely free from seizures at the three month stage.

None of the 27 subjects withdrew during the 3-month treatment period and adverse events were mild and well tolerated. Common adverse events included somnolence, fatigue, decreased appetite, increased appetite and diarrhea.

In five subjects their dose of clobazam was reduced due to its sedative effect.

Conclusions

These preliminary results indicate that CBD significantly reduces the number of seizures in a high proportion of patients that do not respond well to existing AED. The cannabidiol was generally well-tolerated in doses up to 25 mg/kg/day.

It was surprising that in this group of patients which are treatment-resistant such a high number were able to gain an effect. The fact that nearly half of the patients (48%) benefitted from at least a fifty percent reduction in the number of seizures that they suffered from was remarkable.

Furthermore, nearly a quarter (22%) of patients whose seizures were not controlled with at least two anti-epileptic drugs, experienced a reduction of 90% of the number of seizures they were experiencing and 7% were completely seizure free at the end of the 3 month trial period.

Even more remarkable were the results for some defined sub-sets of this generic group and these are set out on Examples 2 to 4 below.

EXAMPLE 2

Efficacy of Cannabidiol in Children and Young Adults with Treatment Resistant Dravet Syndrome Materials and Methods Nine children and young adults with treatment-resistant Dravet syndrome were part of an expanded access compassionate use program for highly purified CBD extract as described in Example 1.

Results

All nine patients with Dravet syndrome were taking at least two concomitant anti-epileptic drugs. These were largely AED operating via GABA and included clobazam; levetiracetam; topiramate; stiripentol; phenobarbital; lacsamide; valproic acid; and zonisamide. The average number of concomitant antiepileptic drugs being taken was 2.7.

The mean number of seizures that these patients suffered from before starting treatment was 35 seizures per month, with a range of 6 to 112 seizures per month recorded.

Efficacy results for the 9 patients are summarized in Table 3 below.

TABLE 2

Changes in Seizure Frequency with CBD Therapy

| All patients | Month 3 (n = 27) |
|---|---|
| Responder rate (>50% reduction) [%] | 13 [48%] |
| Responder rate (>70% reduction) [%] | 11 [41%] |
| Responder rate (>90% reduction) [%] | 6 [22%] |
| Seizure free [%] | 2 [7%] |

TABLE 3

Changes in Seizure Frequency with CBD Therapy in Dravet Syndrome patients

| | Dravet patients (n = 9) | All patients (n = 27) | All patients excluding Dravet patients (n = 18) |
|---|---|---|---|
| Responder rate (>50% reduction) [%] | 5 [56%] | 13 [48%] | 8 [44%] |

TABLE 3-continued

Changes in Seizure Frequency with CBD
Therapy in Dravet Syndrome patients

|  | Dravet patients (n = 9) | All patients (n = 27) | All patients excluding Dravet patients (n = 18) |
|---|---|---|---|
| Responder rate (>70% reduction) [%] | 4 [44%] | 11 [41%] | 7 [39%] |
| Responder rate (>90% reduction) [%] | 3 [33%] | 6 [22%] | 3 [17%] |
| Seizure free [%] | 2 [22%] | 2 [7%] | 0 |

Table 3 shows that after 3 months of therapy, 56% of patients had an equal to or greater than 50% reduction in seizures, a third had a 90% reduction and remarkably 22%, were entirely free from seizures at the three month stage.

None of the 9 subjects withdrew during the 3-month treatment period and adverse events were mild and well tolerated. Common adverse events included somnolence, fatigue, decreased appetite, increased appetite and diarrhea.

Conclusions

These data demonstrate that in this sub-group of patients with treatment-resistant Dravet syndrome a surprisingly high number were able to gain a dramatic reduction in the number of seizures.

Nearly a quarter (22%) of patients were entirely seizure free at the end of the 3 month trial period. This would not be expected in this group of patients who were taking a large number of different anti-epileptic medications and yet were still suffering from a large number of seizures per day.

EXAMPLE 3

Efficacy of Cannabidiol in Children and Young Adults with Treatment Resistant Myoclonic Absence Seizures Materials and Methods Four children and young adults with treatment-resistant myoclonic absence seizures were part of an expanded access compassionate use program for highly purified CBD extract as described in Example 1.

Results

All four patients with myoclonic absence seizures were taking at least two concomitant anti-epileptic drugs. These were largely AED operating via GABA and included clobazam; levetiracetam; topiramate; stiripentol; phenobarbital; lacsamide; valproic acid; and zonisamide. The average number of concomitant antiepileptic drugs being taken was 2.7.

Efficacy results for the four patients are summarized in Table 4 below.

TABLE 4

Changes in Seizure Frequency with CBD Therapy
in patients with myoclonic absence seizures (MAS)

|  | MAS patients (n = 4) | All patients (n = 27) | All patients excluding MAS patients (n = 23) |
|---|---|---|---|
| Responder rate (>50% reduction) [%] | 2 [50%] | 13 [48%] | 11 [48%] |
| Responder rate (>70% reduction) [%] | 2 [50%] | 11 [41%] | 9 [39%] |

TABLE 4-continued

Changes in Seizure Frequency with CBD Therapy
in patients with myoclonic absence seizures (MAS)

|  | MAS patients (n = 4) | All patients (n = 27) | All patients excluding MAS patients (n = 23) |
|---|---|---|---|
| Responder rate (>90% reduction) [%] | 1 [25%] | 6 [22%] | 5 [22%] |
| Seizure free [%] | 0 | 2 [7%] | 2 [9%] |

Table 4 shows that after 3 months of therapy, half of the patients had an equal to or greater than 50% reduction in seizures, one patient (25%) had a 90% reduction at the three month stage.

None of the 4 subjects withdrew during the 3-month treatment period and adverse events were mild and well tolerated. Common adverse events included somnolence, fatigue, decreased appetite, increased appetite and diarrhea.

Conclusions

These data demonstrate that in this sub-group of patients with treatment-resistant MAS a surprisingly high number were able to gain a reduction in the number of seizures.

EXAMPLE 4

Efficacy of Cannabidiol in Children with Treatment Resistant Febrile Infection Related Epilepsy Syndrome (Fires)

Febrile Infection Related Epilepsy Syndrome (FIRES) is a catastrophic epileptic encephalopathy with an unidentified aetiology that comprises a small minority of all patients with refractory status epilepticus.

This syndrome occurs in previously healthy children with 66-100% of survivors becoming developmentally disabled. The mortality rate is up to 30%. There is a critical need for new therapies to treat this condition.

Materials and Methods

Three patients with FIRES, with an age range of from 4 to 15 years, were treated with CBD under an expanded access program as described previously in Example 1.

Safety laboratory studies, physical/neurological exams, 24 hour video/EEG and seizure types and frequencies were assessed at baseline and one month after starting CBD.

A highly purified extract of CBD as an oral solution in sesame oil was used at a concentration of 25 mg/mL.

Treatment was initiated at a dose of 10 mg/kg/day given in two divided doses, increasing by 5 mg/kg/day every 3 days.

Following seizure improvement an average of 2 AEDs were weaned.

Results

Prior to initiation of treatment with highly purified CBD, the patients all suffered from refractory seizures or status epilepticus. These had been treated with anaesthetics including midazolam infusion, pentobarbital infusion, propofol infusion, and isofluorane infusion, additionally patients also were given steroids including lidocaine infusion, and methylprednisolone and other treatments including ketamine, fosphenytoin, thiamine, rituximab, cyclophosphamide, intravenous immunoglobulin, and a hypothermia protocol.

At the time of initiation of CBD, the patients were taking between three and five anti-epileptic drugs including: levetiracetam, clobazam, perampanel, phenobarbital, phenytoin, carbamezapine, felbamate, ketogenic diet, lamotrigine, valproic acid and vagus nerve stimulation therapy.

Baseline 24 hour EEG of seizures were recorded. The total seizures at baseline and during the treatment period are shown in Table 5. Patient 1 was shown to be seizure free after starting treatment for almost all of the treatment period, with the number of seizures being reduced from 7 to 0.3 over a 24 week period. Patient 2 had a 50% reduction in seizures after 4 weeks however the seizure frequency increased after a further 4 weeks then started to decrease again after 16 weeks of treatment. The most remarkable response was seen in Patient 3, who suffered from 5600 seizures at baseline. The number of seizures were dramatically reduced after 4 weeks and at week 24 this patient was still demonstrating a greater than 90% reduction in the number of seizures.

The type of seizures that occurred in the three FIRES patients were all complex partial seizures (focal seizures with impairment). None of the FIRES patients suffered from focal seizures with secondary generalisation or convulsive seizures.

(FIRES) after 12 weeks of treatment which have been described in the Examples 2 to 4 above. In addition the data for the remainder of the patients with other epilepsy syndromes are detailed. These data which exclude the patients with Dravet, MAS and FIRES show a far lower responder rate than for the specified sub-sets of the above specified sub-sets of epilepsy.

In particular, the responder rate for patients obtaining a greater than 90% reduction in their seizures is reduced from 33% in Dravet patients to only 8% in the unspecified group. This suggests that patients suffering from a TRE of sub-type Dravet syndrome, myoclonic absence seizures or FIRES will respond better to treatment with highly purified CBD than patients with other epilepsy sub-types.

TABLE 5

Total Seizure Data

| Visit | Frequency (per month) | Change from Baseline | % Change from Baseline | Responder (>=50% Reduction) | Responder (>=70% Reduction) | Responder (>=90% Reduction) | Seizure Free |
|---|---|---|---|---|---|---|---|
| Patient 1 | | | | | | | |
| BL | 4.0 | n/a | n/a | n/a | n/a | n/a | n/a |
| Wk 4 | 0.0 | −4.0 | −100.0 | Yes | Yes | Yes | Yes |
| Wk 8 | 1.0 | −3.0 | −75.0 | Yes | Yes | No | No |
| Wk 12 | 0.0 | −4.0 | −100.0 | Yes | Yes | Yes | Yes |
| Wk 16 | 0.0 | −4.0 | −100.0 | Yes | Yes | Yes | Yes |
| Wk 24 | 0.3 | −3.7 | −92.0 | Yes | Yes | Yes | No |
| Patient 2 | | | | | | | |
| BL | 7.0 | n/a | n/a | n/a | n/a | n/a | n/a |
| Wk 2 | 0.8 | −6.2 | −88.6 | Yes | Yes | No | No |
| Wk 4 | 3.0 | −4.0 | −57.1 | Yes | No | No | No |
| Wk 8 | 10.0 | 3.0 | 42.9 | No | No | No | No |
| Wk 12 | 8.0 | 1.0 | 14.3 | No | No | No | No |
| Wk 16 | 4.0 | −3.0 | −42.9 | No | No | No | No |
| Patient 3 | | | | | | | |
| BL | 5600.0 | n/a | n/a | n/a | n/a | n/a | n/a |
| Wk 4 | 47.2 | −5552.8 | −99.2 | Yes | Yes | Yes | No |
| Wk 8 | 9.2 | −5590.8 | −99.8 | Yes | Yes | Yes | No |
| Wk 12 | 141.6 | −5458.4 | −97.5 | Yes | Yes | Yes | No |
| Wk 24 | 542.0 | −5058.0 | −90.3 | Yes | Yes | Yes | No |

Follow up laboratory tests showed no changes in safety studies or concomitant AED levels. No treatment related adverse effects were observed.

Conclusions

CBD treatment was very well tolerated and associated with a dramatic and nearly immediate greater than 90% improvement in clinical and electrographic seizure burden in two of the three children with refractory seizures or status epilepticus due to FIRES.

After a reduction in seizures the patients were able to walk and verbalise once more.

SUMMARY TABLE AND CONCLUSIONS

Table 6 below summarises the data obtained in the three sub-sets: Dravet syndrome; myoclonic absence seizures (MAS) and febrile infection related epilepsy syndrome

TABLE 6

Changes in Seizure Frequency with CBD Therapy in patients with sub-type TRE and all patients excluding the sub-types.

| | All patients (excluding Dravet, MAS and FIRES) (n = 13) | Dravet patients (n = 9) | MAS patients (n = 4) | FIRES patients (n = 3) |
|---|---|---|---|---|
| Responder rate (>50% reduction) [%] | 5 [38%] | 5 [56%] | 2 [50%] | 2 [67%] |
| Responder rate (>70% reduction) [%] | 4 [31%] | 4 [44%] | 2 [50%] | 2 [67%] |
| Responder rate (>90% reduction) [%] | 1 [8%] | 3 [33%] | 1 [25%] | 2 [67%] |
| Seizure free [%] | 0 | 2 [22%] | 0 | 1 [33%] |

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." *Expert Review of Neurotherapeutics* 12 (12): 1419-27.

Kwan P, Arzimanoglou A, Berg A T, Brodie M J, Hauser W A, Mathern G, Moshé S L, Perucca E, Wiebe S, French J. (2009) "Definition of drug resistant epilepsy: Consensus proposal by the ad hoc Task Force of the ILAE Commission on Therapeutic Strategies." *Epilepsia.*

Mechoulam R and Carlini E A (1978). "Toward drugs derived from *cannabis*." Die naturwissenschaften 65:174-9.

Porter B E, Jacobson C (December 2013). "Report of a parent survey of cannabidiol-enriched *cannabis* use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia.* 52 Suppl 7: 2-26

The invention claimed is:

1. A method of treating treatment-resistant epilepsy comprising administering cannabidiol (CBD) to a subject in need thereof, wherein the epilepsy is status epilepticus due to febrile infection related epilepsy syndrome (FIRES).

2. The method of claim 1, wherein the CBD is administered in combination with two or more concomitant anti-epileptic drugs (AED).

3. The method of claim 2, wherein the seizure type to be treated is a complex partial seizure (focal seizure with impairment).

4. The method of claim 2, wherein the CBD is administered in an amount that reduces total convulsive seizure frequency by greater than 70% with respect to the seizure frequency achieved on the concomitant anti-epileptic drugs (AED).

5. The method of claim 2, wherein the CBD is administered in an amount that reduces total convulsive seizure frequency by greater than 90% with respect to the seizure frequency achieved on the concomitant anti-epileptic drugs (AED).

6. The method of claim 2, wherein the CBD is administered in an amount that reduces total convulsive seizure frequency by 100% with respect to the seizure frequency achieved on the concomitant anti-epileptic drugs (AED).

7. The method of claim 1, wherein the CBD is a highly purified extract of *cannabis* which comprises at least 98% (w/w) CBD.

8. The method of claim 2, wherein the two or more concomitant anti-epileptic drugs (AED) are administered in combination with the CBD at a dose that is reduced from a recommended therapeutic dose without CBD.

9. The method of claim 8, wherein the dose of AED which is reduced is of clobazam.

10. The method of claim 1, wherein the dose of CBD is from 5 mg/kg/day to 25 mg/kg/day.

11. The method of claim 1, wherein the dose of the CBD is at least 5 mg/kg/day.

12. The method of claim 1, wherein the dose of the CBD is at least 10 mg/kg/day.

13. The method of claim 1, wherein the dose of the CBD is at least 15 mg/kg/day.

14. The method of claim 1, wherein the dose of the CBD is at least 20 mg/kg/day.

* * * * *

UNITED STATES PATENT AND TRADEMARK OFFICE
CERTIFICATE OF CORRECTION

Page 1 of 1

PATENT NO. : 9,949,936 B2
APPLICATION NO. : 15/284766
DATED : April 24, 2018
INVENTOR(S) : Guy et al.

It is certified that error appears in the above-identified patent and that said Letters Patent is hereby corrected as shown below:

In the Specification

At Column 1, Lines 6:
"Related Application
This application is a continuation of U.S. application Ser. No. 14/741,783, filed Jun. 17, 2015, which claims the benefit of GB 1506550.1and GB 1410771.8, the content of each of which is incorporated by reference herein in its entirety."
Should read:
--Cross-Reference to Related Applications
This application is a continuation of U.S. application Ser. No. 14/741,783, filed Jun. 17, 2015, which claims the benefit of GB 1506550.1, filed Apr. 17, 2015, and GB 1410771.8, filed Jun. 17, 2014, the content of each of which is incorporated by reference herein in its entirety.--

Signed and Sealed this
Thirtieth Day of June, 2020

Andrei Iancu
*Director of the United States Patent and Trademark Office*